United States Patent [19]

Yaniv

[11] Patent Number: 4,966,147

[45] Date of Patent: Oct. 30, 1990

[54] METHOD FOR THE DIAGNOSIS OF ALLERGIC RHINITIS

[76] Inventor: Eitan Yaniv, 28 Rambam Street, Ra'anana, Israel

[21] Appl. No.: 341,873

[22] Filed: Apr. 24, 1989

[51] Int. Cl.$^5$ .............................................. A61B 5/00
[52] U.S. Cl. .................................... 128/630; 128/743; 128/774
[58] Field of Search ............... 128/630, 743, 774, 897, 128/898, 17; 604/54

[56] References Cited

U.S. PATENT DOCUMENTS 4,243,651 7/1981 Nalebuff .............................. 128/743

Primary Examiner—Randall L. Green
Assistant Examiner—Randy Shay
Attorney, Agent, or Firm—Benjamin J. Barish

[57] ABSTRACT

A method for the diagnosis of allergic rhinitis in a patient, comprises visually observing the size of the patient's nasal airway, administering a solution of up to 0.5% histamine to the patient's nasal airway, and after a predetermined time interval, again visually observing the size of the patient's nasal airway to determine whether or not it has become substantially blocked, the blocking of the patient's nasal airway indicating the patient is suffering from allergic rhinitis. Also described is a kit for the diagnosis of allergic rhinitis in a patient, comprising a first nasal spray container containing a solution of 0.05% histamine; and a second nasal spray container containing a solution of 0.5% histamine.

10 Claims, 1 Drawing Sheet

METHOD FOR THE DIAGNOSIS OF ALLERGIC RHINITIS

BACKGROUND OF THE INVENTION

The present invention relates to a method, and also to a kit, for the diagnosis of allergic rhinitis.

Rhinitis is an inflammation of the mucous membrane that lines the nose, producing a watery discharge. It may be caused by an infection (e.g., common cold), by an allergy (e.g., hayfever), or by an unknown cause (e.g., vasometer rhinitis). The diagnosis of infectious rhinitis can usually be done without difficulty, but it is more problematic to distinguish between allergic rhinitis from non-allergic rhinitis. The techniques presently used usually involve measuring nasal airway resistance by equipment which is relatively expensive and requires expertise for operation, and which is therefore generally not available in the offices of physicians or smaller clinics. Failure to distinguish between allergic rhinitis and non-allergice rhinitis also causes difficulties in determining whether or not a particular rhinitis condition is treatable at all, or whether a particular treatment administered to the patient has been effective, particularly in the case of children which tend to deny that they are suffering from a disease.

OBJECTS AND SUMMARY OF THE INVENTION

An object of the present invention is to provide a method for the diagnosis of allergic rhinitis. Another object of the invention is to provide a kit which may be used for diagnosing allergic rhinitis in accordance with the present invention.

According to the present invention, there is provided a method for the diagnosis of allergic rhinitis in a patient, comprising: examining the size of the patient's nasal airway; administering histamine to the patient's nasal airway; and after a predetermined time interval, reexamining the size of the patient's nasal airway to determine whether or not it has become substantially blocked, the blocking of the nasal airway indicating the patient is suffering from allergic rhinitis.

Good results have been obtained when the histamine is administered as a solution of up to 0.5% histamine. Preferably, the histamine is administered in two steps. First, it is administered as a solution of 0.05% histamine, and if blockage is not observed during the reexamination, it is then administered as a solution of 0.5% histamine.

Best results have been obtained when the predetermined time interval after administering the histamine before reexamining the size of the patient's nasal air passageway is approximately four minutes.

The histamine may be administered in the form of a nasal spray, and the examination and reexamination may both be performed by direct visual observation. This enables the diagnostic method to be performed quickly and simply by a physician, without expensive equipment or any special expertise. The physician is thus able to obtain substantially immediate results, thereby enabling the physician to determine not only whether a particular rhinitis condition is treatable, but also the efficacy of the treatment given to the patient. That is, after the patient has been treated for rhinitis, the above diagnostic method may be performed, whereupon a substantial blockage of the nasal airway will indicate that the patient is still suffering from allergic rhinitis, and therefore that the treatment given the patient was not effective.

The invention also provides a kit for the diagnosis of allergic rhinitis in a patient, comprising: a first nasal spray container containing a solution of 0.05% histamine; and a second nasal spray container containing a solution of 0.5% histamine. In most case, the examination and reexamination of the patient's nasal airway can be effected by direct visual observation without the need for a nasal speculum, but the kit may also include a nasal speculum having a scale for measuring the spacing between the jaws of the speculum.

Further features and advantages of the invention will be apparent from the description below.

BRIEF DESCRIPTION OF THE DRAWINGS

The invention is herein described, by way of example only, with reference to the accompanying drawings, wherein:

FIG. 3 is a photographic print illustrating a patient's left nostril before the test;

FIG. 4 is a photographic print illustrating the patient's left nostril of the same patient as FIG. 3 after histamine has been administered and the patient has reacted positively, indicating the patient is suffering from allergic rhinitis; and FIGS. 5 and 6 are photographic prints corresponding to FIGS. 3 and 4, but of the patient's right nostril.

Figure 1:
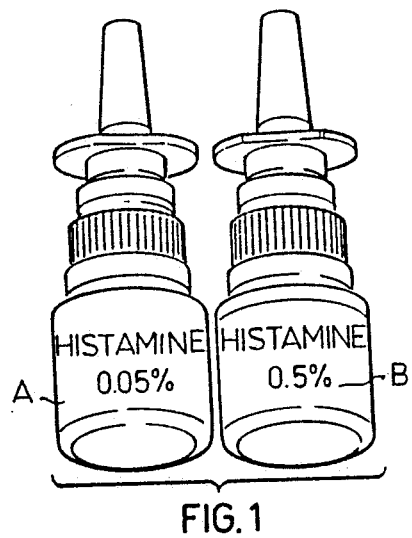
FIG. 1 illustrates two nasal spray containers containing solutions of histamine to be included in a kit that may be supplied to physicians to enable them to diagnose allergic rhinitis in a patient in accordance with the method of the present invention.

DESCRIPTION OF A PREFERRED EMBODIMENT 84 patients between the ages 9 and 65 suffering from rhinitis, and 20 individuals without any nasal or other allergic symptons, were tested with histamine test. A thorough medical history was taken from each, and physical examinations were performed. The nose was carefully examined, and the open condition of the basal airways was observed by direct visual observation, as seen in FIGS. 3 and 5. Blood levels for eosinophils and IgE were taken and nasal smears for eosinophils checked.

The histamine test was then performed with solutions of histamine 0.01%, 0.025%, 0.05%, 0.1%, 0.25%, 0.5%, and 1%. Administered into the nose as a spray in a volume of 0.3 ml (i.e., doses of 0.03 mg, 0.075 mg, 0.15 mg, 0.3 mg, 0.75 mg, 1.5 mg, 3 mg). During the test patients were asked whether the spray caused any irritation. The appearances of sneezing and rhinitis were noted.

Four minutes after administration of the spray the nose was examined—specifically the colour of the mucous membrane and the size of the conchae as well as the extent of an obstructed airway. The next dose of histamine was then administered until the mucosae of the conchae became so swollen that they impinged on the septum, thus practically blocking the airway.

All patients had been instructed to stop anti-allergic treatement and nasal drops for at least a week prior to the test (most subjects were without treatment for a longer period of time). On completion of the test, anti-allergic treatment was started and a second histamine test performed three weeks later.

The main parameter considered during the histamine test was the appearance of mucosal swelling and blockage of the airway. The test was considered positive when it led to blockage of the airway, as seen in FIGS. 4 and 6.

Nasal irritation and change in the colour of musosa were noted, but little correlation between these parameters and the test was found. Rhinitis and sneezing were significant, but as minor signs only.

Patients were divided into three groups according to the results of the histamine test:

Group A 54 patients who responded to a dose of histamine up to 0.05%; they were considered sensitive.

Group B 21 patients who responded to a dose of histamine up to 0.5%; they were considered mildly sensitive.

Group C 9 patients, together with 20 healthy subjects who were a control group, responded to a dose of 1% histamine, or failed to respond altogether; they were considered insensitive to the test.

All patients (excluding the control group) were started on treatment with beclamethasone nasal spray and oral anti-histamine.

The first 18 patients were randomly given three different anti-histamines (Astemizole, Mebhydroline, Chlorpheniramine, Nalate). From the nineteenth patient onwards, the anti-histamine of choice was astemizole 10 mg.

After three weeks of treatment, a second histamine test was performed and patients were asked to describe the response to treatment (specifically rhinitis and blocked nose) by choosing one of the following: (a) no change; (b) better; (c) much better; and (d) healthy.

A very good correlation was found between the patients' subjective assessments of their condition and the results of a second histamine test; e.g., when a patient noted "no change" his reaction to histamine was similar to that before treatment. On the other hand, when he considered himself "much better", a dose of at least 1% histamine was required to product a reaction.

The best response to the treatment was found in Group A. 84% of these patients improved significantly. In this group only 9 patients did not improve significantly. In 6 of them, a change of anti-histamine brought about an improvement—both subjectively and in regard to histamine test.

In Group B, 24% of the subjects responded well to treatment; 43% responded moderately and; no response was demonstrated in 33%.

In Group C only 1 patient (11%) responded to treatment. A deviated septum was found in 52% of the non-responsive patients.

The levels of IgE in patients' serum ranged from 12 u/ml to 124 u/ml (except for two readings of 410 u/ml and 440 u/ml). There was no significant difference between patients suffering from rhinitis and the control group.

Blood eosinophil counts and eosinophil counts in nasal smears could not differentiate patients with rhinitis from the control group.

The novel diagnostic method may therefore be performed in only two steps, wherein the histamine is first administered as a solution of 0.05% histamine and, if blockage does not occur, it is then administered as a solution of 0.5% histamine. Blockage occurring upon the administration of 0.05% histamine indicates a high degree of allergic rhinitis, and therefore it would be expected that the patients would respond best to treatment. Many preparations are available for treating allergic rhinitis, and the treatment would therefore involve selecting the most effacacious preparation. The above-described diagnostic method may be applied after each treatment, since a positive reaction (i.e., blockage of the nasal airway) will indicate that the patient is still suffering from allergic rhinitis, and therefore that the treatment was not particularly effective.

If no positive reaction is exhibited to the administration of 0.05% histamine, then the 0.5% histamine should be administered since a positive reaction (blockage of the nasal airway) to this concentration also indicates the presence of allergic rhinitis. If no positive reaction is produced after the administration of 0.5% histamine, then it may be concluded that the rhinitis condition is not an allergic rhinitis.

Thus, a physician may be supplied with a kit containing only the two nasal spray containers illustrated in FIG. 1, container A including a solution of 0.05% histamine, and container B containing a solution of 0.5% histamine.

FIG. 3 illustrates the left nostril of a patient before the test, wherein the septum (S) is spaced from the inferior concha (I), thereby enabling the middle concha (M) to be seen. FIG. 4 illustrates the same nostril after the histamine has been administered and a positive reaction has been produced (that is the nasal airway has become substantially blocked), wherein it will be seen that the inferior concha (I) touches the septum (S), thereby blocking the middle concha (M). Such a patient, therefore would be diagnosed as having allergic rhinitis.

FIGS. 5 and 6 are views similar to views FIGS. 3 and 4, respectively, but illustrating the right nostril of the same patient.

Figure 2:
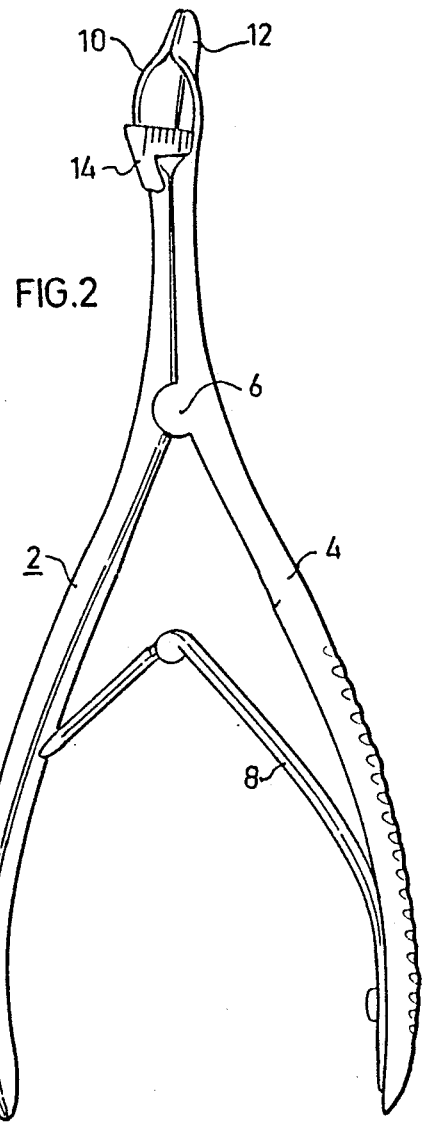
FIG. 2 illustrates a nasal speculum which may be included in the kit.

It will thus be seen that the condition of the nasal airway can be examined by the physician by direct visual observation. However, it may be desirable to include, in the kit, a nasal speculum, such as illustrated in FIG. 2, of conventional construction including two handles 2, 4 pivotally mounted at 6 and spring-urged to their closed condition by spring 8, the handles terminating in a pair of jaws 10, 12 instead of into the patient's nose. Such a conventional nasal speculum may be used in the diagnostic method, since the blocking of the nasal airway can be directly visually observed. However, it may be desirable to include a scale, shown at 14, fixed to one of the jaws 10 and cooperable with respect to the other jaw 12, to measure the size of the nose airway both before and after the administration of the histamine.

Many other variations of the invention will be apparent.

What is claimed is:

1. A method for the diagnosis of allergic rhinitis in a patient, comprising:
    examining the size of the patient's nasal airway;
    administering histamine to the patient's nasal airway; and
    after a predetermined time interval, reexamining the size of the patient's nasal airway to determine whether or not it has become substantially blocked, the blocking of the nasal airway indicating the patient is suffering from allergic rhinitis.

2. The method according to claim 1, wherein said histamine is administered as a solution of up to 0.5% histamine.

3. The method according to claim 1, wherein the histamine is first administered as a solution of 0.05% histamine, and if blockage is not observed during the reexamination, the histamine is then administered as a solution of 0.5% histamine.

4. The method according to claim 2, wherein said predetermined time interval is approximately four minutes.

5. The method according to claim 2, wherein the histamine is administered in the form of a nasal spray.

6. The method according to claim 1, wherein said examination and reexamination are performed by direct visual observation.

7. A method for the diagnosis of allergic rhinitis in a patient, comprising:

visually observing the size of the patient's nasal airway;

administering a solution of up to 0.5% histamine to the patient's nasal airway; and after a predetermined time interval, again visually observing the size of the patient's nasal airway to determine whether or not it has become substantially blocked, the blocking of the patient's nasal airway indicating the patient is suffering from allergic rhinitis.

8. The method according to claim 7, wherein the histamine is first administered as a solution of 0.05% histamine, and if blockage is not observed during the reexamination, the histamine is then administered as a solution of 0.5% histamine.

9. The method according to claim 7, wherein said predetermined time interval is approximately four minutes.

10. The method according to claim 7, wherein the histamine is administered in the form of a nasal spray.

* * * * *